United States Patent
McKay

(10) Patent No.: US 8,470,046 B2
(45) Date of Patent: Jun. 25, 2013

(54) BONE AUGMENTATION DEVICE AND METHOD

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/093,144

(22) Filed: Apr. 25, 2011

(65) Prior Publication Data

US 2012/0270172 A1    Oct. 25, 2012

(51) Int. Cl.
*A61F 2/02* (2006.01)

(52) U.S. Cl.
USPC ........................................ 623/17.18; 433/173

(58) Field of Classification Search
USPC .................... 433/173, 174; 623/17.18, 17.19, 623/16.11, 23.53, 23.56; 606/264, 77
See application file for complete search history.

(56) References Cited

U.S. PATENT DOCUMENTS

| | | | |
|---|---|---|---|
| 4,356,572 A | 11/1982 | Guillemin et al. | |
| 4,531,916 A | 7/1985 | Scantlebury et al. | |
| 4,787,906 A | 11/1988 | Haris | |
| 5,417,569 A | 5/1995 | Perisse | |
| 5,433,607 A | 7/1995 | Schmid et al. | |
| 5,470,230 A | 11/1995 | Daftary et al. | |
| 5,509,765 A | 4/1996 | Albin | |
| 5,562,735 A * | 10/1996 | Margulies | 601/61 |
| 5,824,088 A | 10/1998 | Kirsch | |
| 5,839,899 A | 11/1998 | Robinson | |
| 5,863,200 A | 1/1999 | Hamada et al. | |
| 5,931,674 A | 8/1999 | Hanosh et al. | |
| 5,951,288 A | 9/1999 | Sawa | |
| 5,971,987 A | 10/1999 | Huxel et al. | |
| 6,030,218 A | 2/2000 | Robinson | |
| 6,227,860 B1 | 5/2001 | Hobo | |
| 6,293,950 B1 | 9/2001 | Lynch et al. | |
| 6,328,765 B1 | 12/2001 | Hardwick et al. | |
| 6,402,518 B1 | 6/2002 | Ashman | |
| 6,409,764 B1 | 6/2002 | White et al. | |
| 6,572,655 B1 | 6/2003 | Johnson | |
| 6,863,530 B2 | 3/2005 | McDevitt | |
| 6,916,321 B2 | 7/2005 | TenHuisen et al. | |
| 6,991,461 B2 | 1/2006 | Gittleman | |
| 7,179,088 B2 | 2/2007 | Schulter et al. | |
| 7,300,439 B2 | 11/2007 | May | |
| 7,455,674 B2 | 11/2008 | Rose | |
| 7,855,062 B2 | 12/2010 | Harlow et al. | |
| 2005/0267478 A1 | 12/2005 | Corradi et al. | |
| 2008/0221681 A1 * | 9/2008 | Trieu et al. | 623/11.11 |
| 2009/0176193 A1 | 7/2009 | Kaigler, Sr. | |
| 2010/0217331 A1 | 8/2010 | Spagnoli et al. | |
| 2011/0014587 A1 | 1/2011 | Spagnoli et al. | |

(Continued)

OTHER PUBLICATIONS www.osteotech.com/prodgraftech.shtm Medtronic Now with Osteotech An unprecedented biologic and regenerative therapy portfolio GRAFTECH Product Sheet.

(Continued)

*Primary Examiner* — Bruce E Snow
(74) *Attorney, Agent, or Firm* — Sorell Lenna & Schmidt LLP

(57) ABSTRACT

A bone augmentation device includes at least one axial member defining a longitudinal axis and a plurality of transverse members. Each transverse member extends from a first end, or removably connected to the at least one axial member to a second end configured for fixation with bone. The transverse members are spaced apart and disposed along the longitudinal axis. The at least one axial member and the transverse members are disposed in a configuration to define a bone graft cavity. Methods of use are also disclosed.

14 Claims, 12 Drawing Sheets

OTHER PUBLICATIONS www.osteotech.com/proddowel.shtm Medtronic Now with Osteotech An unprecedented biologic and regenerative therapy portfolio Graftech Cervical Dowel.

www.osteotech.com/prodantpostfaq.shtm Medtronic Now with Osteotech An unprecedented biologic and regenerative therapy portfolio Graftech Lumbar Allografts Frequently Asked Questions.

* cited by examiner

BONE AUGMENTATION DEVICE AND METHOD

TECHNICAL FIELD

The present disclosure generally relates to medical devices for the treatment of bone disorders, for example, periodontal disorders, and more particularly to a bone augmentation device and method including a scaffold configuration of axial and transverse members for augmenting bone that does not require removal.

BACKGROUND

Surgical repair and/or reconstruction procedures including those employing implants are widely used in dental and oral surgery for restoration of the jaw anatomy. These procedures are often used to treat bone defects and disorders of the jaw, which may result and/or be caused from periodontal diseases, bone, gum and/or tooth loss, trauma, tumors, infections and other complications. New bone growth is often desired to repair a defect or to build up the jawbone so that sufficient bone exists to embed and retain an implant.

In some cases, a ridge augmentation procedure is employed to add bone to the jaw so that sufficient alveolar bone exists for implant and/or tooth retention. Such procedures can employ a spacing device to facilitate bone growth. After new bone has formed, the devices employed during the augmentation are removed. However, the removal of these devices can cause tissue disruption that undesirably exposes new bone and disrupts vascularity, or can be difficult to remove due to bone overgrowth. This disclosure describes an improvement over these prior art technologies.

SUMMARY OF THE INVENTION

Accordingly, a bone augmentation device and method is provided for treating bone disorders, for example, periodontal disorders. It is contemplated that the bone augmentation device includes a scaffold configuration of axial and transverse members for augmenting bone, at least part of the device being formed from biologically absorbable or biodegradable material. It is further contemplated that the bone augmentation device is configured to promote bone growth. At least part of the bone augmentation device is absorbed into the newly formed bone. As such, the need for disassembly and removal of the absorbed portion of the device is eliminated, and disruption of gingival tissue and vascularity is reduced or minimized.

In one particular embodiment, in accordance with the principles of the present disclosure, a bone augmentation device is provided. The bone augmentation device includes an axial member defining a longitudinal axis, and a plurality of transverse members having a first end coupled to the axial member. Each of the transverse members extends from the first end to a second end configured for direct fixation with bone tissue. The transverse members are spaced apart and are disposed along the longitudinal axis in a transverse orientation relative to the longitudinal axis. The axial member and the transverse members are disposed in a configuration to define a bone graft cavity. At least the transverse members are formed of biologically absorbable material.

In one embodiment, a bone augmentation device kit is provided. The kit includes at least one structure selected from the following group: i) a horizontal strut defining a longitudinal axis, and a plurality of vertical struts configured to be coupled to the horizontal strut and extend therefrom to a distal end having a linear configuration and configured for direct fixation with jaw bone tissue, the vertical struts being configured to be disposed in series along the longitudinal axis during fixation; and ii) a horizontal strut defining a longitudinal axis, and a plurality of vertical struts coupled to the horizontal strut and extending therefrom to a distal end having a linear configuration and configured for direct fixation with bone tissue, the vertical struts being disposed in series along the longitudinal axis. The kit also includes bone graft material. The kit can also be provided in a sterilized or in the alternative be provided in a sterilizable packaging. A tool for implementing the bone augmentation device of the present invention can also be included in the kit. The horizontal strut and the vertical struts are disposed or disposable in a scaffold configuration to define a cavity disposed between the horizontal strut and the bone and configured for disposal of the bone graft material. At least the vertical struts of the bone augmentation device are formed of biologically absorbable material.

In one embodiment, a biologically absorbable implantable fastener for maintaining space during bone grafting procedures in a patient in need of such treatment is provided. The biologically absorbable fastener includes an arcuate first end configured for coupling to an axial member defining a longitudinal axis, a linear second end disposed opposite the arcuate first end, and a shaft extending between the arcuate first end and the linear second end. The linear second end is configured for direct fixation in bone tissue, including wherein the linear second end is configured to penetrate the bone tissue and is selected from a pointed second end and a threaded second end.

In one embodiment, a method of augmenting bone tissue at a surgical site is provided. The method includes implanting at least one of the presently disclosed and claimed structures at least partially into the bone tissue, depositing bone graft material about the implanted structure, allowing the bone graft material to form bone tissue, and allowing biologically absorbable material of the structure to be absorbed or remodeled into the newly formed bone tissue.

BRIEF DESCRIPTION OF THE DRAWINGS

The present disclosure will become more readily apparent from the specific description accompanied by the following drawings, in which.

DETAILED DESCRIPTION OF THE INVENTION

Figure 1:
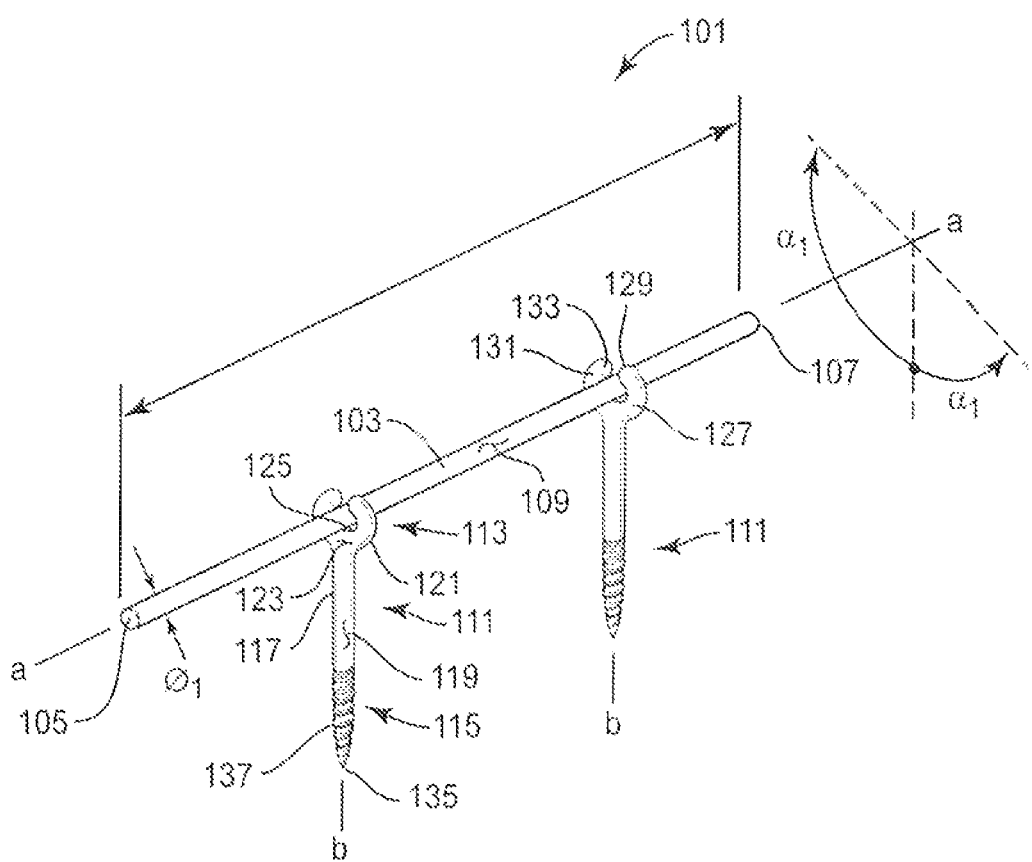
FIG. 1 is a perspective view of one particular embodiment of a bone augmentation device in accordance with the principles of the present disclosure.

The exemplary embodiments of the bone augmentation device and methods of use disclosed are discussed in terms of medical devices for the treatment of bone disorders, for example, periodontal disorders, and more particularly, in terms of a bone augmentation device and method including a scaffold configuration of axial and traverse members for augmenting bone. At least part of the bone augmentation device of the present disclosure is made from bioabsorbable material that is absorbed or remolded into new bone that does not require removal but instead is reabsorbed at the site of implantation. In one embodiment of the present invention the bioabsorbable material used is a unique bone-collagen or ceramic-collagen composite that is absorbed or remodeled into newly formed bone around the bone augmentation device of the present invention. f Since at least part of the bone augmentation device of the present disclosure is made from bioabsorbable material that does not have to be removed, it avoids many of, if not all, of the issues associated with removal of non-bioabsorbable mesh devices that have to be removed after implantation.

As stated above, at least some components of the bone augmentation device of the present disclosure are made of non-bioabsorbable materials that may have to be removed after they have been used. However, since only some components of the device have to be removed, this can be done with minimal tissue and vascular disruption. It is envisioned that the bone augmentation device is configured to maintain in the area of implantation when growing new bone either in a defect and/or when building up a jawbone in a ridge augmentation procedure. It is further envisioned that the bone augmentation device of the present disclosure is employed with a surgical implant so as to add bone height and/or width to the jaw so that sufficient bone exists to embed and retain an implant, while preventing overlying soft tissue and muscle forces from compressing newly forming bone. It is contemplated that the bone augmentation device of the present invention may be a scaffolding device made form bone/collagen or ceramic-collagen composite material that includes one or more integral or interlocking struts, which provide mechanical support to newly forming bone underneath it. Some components of the device can be made of other non-bioabsorbable materials.

It is envisioned that the present disclosure may be employed to treat periodontal disorders such as, for example, peri-implantitis, chronic, aggressive and necrotizing periodontitis, gingivitis, other periodontal diseases, and oral maxillofacial bone defects due to trauma or disease. It is contemplated that the present disclosure may be employed with other osteal and bone related applications, including those associated with diagnostics and therapeutics. The system and methods of the present disclosure may also be used on animals, in particular mammals, including humans, as well as on bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

The following discussion includes a description of a bone augmentation device and related methods of employing the bone augmentation device in accordance with the principles of the present disclosure. Alternate embodiments are also disclosed. Reference will now be made in detail to the exemplary embodiments of the present disclosure, which are illustrated in the accompanying figures. Turning now to FIG. 1, there is illustrated components of a bone augmentation device 101 in accordance with the principles of the present disclosure The components of bone augmentation device 101 are fabricated from materials suitable for medical applications, including allograft material such as, nondemineralized bone, substantially fully demineralized bone, partially demineralized bone, superficially demineralized bone or combinations thereof with some structural properties developed and marketed by Osteotech, Inc, as described in U.S. Pat. Nos. 6,440, 444; and 6,696,073 and U.S. patent application Ser. Nos. 11/047,992 and 11/934,980; each of which are incorporated herein in their entirety by reference; ceramics, natural polymers, collagen, biocompatible materials, biodegradable materials, biologically absorbable materials, bioerodable materials, bone, autograft, metal, polymers and/or their composites, depending on the particular application and/or preference of a medical practitioner. For example, the components of the bone augmentation device 101, individually or collectively, can be fabricated from materials such as biocompatible materials such as natural polymers including collagen, ceramics, metals and plastic such as stainless steel, titanium, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, rigid polymers including polyphenylene, polyamide, polyimide, polyetherimide, polyethylene epoxy, and composites thereof. Bioabsorbable materials used can be selected from the following polymers: PLA, PLLA, PDLA, PGA, PET, PTFE, PCU, PU, and combinations thereof. Various components of the bone augmentation device 101 may have material composites, including the above materials, to achieve various desired characteristics such as strength, rigidity, elasticity, compliance, biomechanical performance, durability and radiolucency or imaging preference. The components of bone augmentation device 101 can be made of radiolucent materials such as polymers. Radiomarkers may be included for identification under x-ray, fluoroscopy, CT or other imaging techniques.

The bone augmentation device 101 is configured for treating bone disorders, for example, of the jawbone where new bone growth is desired to repair a defect and/or build up the jawbone for implant retention. The components of the bone augmentation device 101 are configured to augment bone. To the extent the components of the bone augmentation device 101 are intended or designed to be removed from existing or new bone tissue, they are configured to be absorbed or remodeled into the newly forming bone or removed therefrom with minimal disruption to soft tissue and vasculature, as will be described.

The bone augmentation device 101 includes an axial member, such as, for example, a horizontal strut 103. The horizontal strut 103 defines a longitudinal axis a. The horizontal strut 103 extends from a first end 105 to a second end 107, and has an outer surface 109.

The horizontal strut 103 extends along the longitudinal axis a from the first end 105 to the second end 107, defining an axial length I. Other configurations are possible. For example, it is envisioned that all or a portion of horizontal strut 103 may be offset, staggered and/or disposed at an angle from the longitudinal axis a.

The outer surface 109 of the horizontal strut 103 has a smooth or even configuration such that horizontal strut 22 may easily pass through tissue, the term tissue as used herein at least including soft tissue, cartilage, and/or bone tissue. Other configurations are possible. For example, it is contemplated that all or a part of the outer surface 109 may be rough, textured, porous, semi-porous, dimpled and/or polished.

The first and second ends 105, 107 are configured for enclosure within tissue. In addition, and/or in the alternative, it is envisioned that the first and second ends 105, 107 may be configured for attachment to tissue, which may include fixation, adhesive, instrumentation such as a brace or clip, and/or tissue penetration. It is envisioned that one or both of the first and second ends 105, 107 may be attached with tissue for a particular application.

The horizontal strut 103 has a solid, cylindrical configuration and has a thickness, such as, for example, a diameter $\phi_1$. The diameter $\phi_1$ has a relatively thin or reduced dimension such that the horizontal strut 103 may easily pass through tissue. It is envisioned that the diameter $\phi_1$ may be in a range of approximately 1 to 3 millimeters (mm). It is further envisioned that the cross-sectional geometry of the horizontal strut 103 may have various configurations, such as, for example, round, oval, oblong, triangular, polygonal having planar or arcuate sides, irregular, uniform, non-uniform, consistent or variable, and/or all or a portion of the horizontal strut 103 may be porous, perforated, tubular or articulate.

The bone augmentation device 101 includes a plurality of transverse members, such as, for example, a series of bone fasteners 111 coupled to the horizontal strut 103 for treating and conforming to a selected portion of a jawbone at a surgical site according to the requirements of the jaw anatomy and/or a particular application, as discussed further below. The bone fasteners 111 axially extend in a parallel orientation and are arranged in a series, spaced apart along the horizontal strut 103 and the axis a to support the horizontal strut 103. It is envisioned that the bone fasteners 111 may extend in various orientations such as arcuate, undulating, orthogonal (such as, for example, orthogonal with respect to the horizontal strut 103 as shown in FIG. 1), stepped, staggered and/or intermittent with spaced apart ends.

The bone augmentation device of the present invention may be configured so that the transverse members are disposed in a parallel orientation during fixation with bone and/or each of the transverse members includes a pointed second end, and/or each of the transverse members is of unitary construction with the axial member and/or each of the transverse members is of unitary construction with the axial member. Each of these devices may be configured so that the axial member and the transverse members define the bone graft cavity.

The horizontal strut 103 and the bone fasteners 111 of the bone augmentation device 101 are arranged in a configuration to define a bone graft cavity (see, for example, FIG. 5, as discussed further below). It is contemplated that the bone augmentation device 101 may include a plurality of horizontal struts 103, and/or a plurality of axially-arranged series of bone fasteners 111, the number of which may correspond to the number of horizontal struts 103 included in the bone fastener 111. It is envisioned that all or a portion of the horizontal strut 103 may be flexible or elastically or plastically deformable such that the horizontal strut 103 is adjustable or can be modified to conform to a selected portion of jawbone for a particular surgical application. It is further envisioned that the horizontal strut 103 may be formed from a rigid or semi-rigid material to increase the strength of the bone augmentation device 101 and/or the integrity of the bone graft cavity. In an embodiment in accordance with the present disclosure, the horizontal strut 103 is formed from at least one of stainless steel and titanium.

Each of the bone fasteners 111 defines a transverse axis b, relative to longitudinal axis a. It is envisioned that all or a portion of the bone fastener 111 may be offset, staggered and/or disposed at an angle from longitudinal axis b. It is further envisioned that axis b may be transverse to axis a and disposed at an orientation in a plurality of planes about the horizontal strut 103 including for example, perpendicular, acute, obtuse, and/or in a range between 0 and 360 degrees, according to the requirements of a particular application.

The bone fastener 111 includes a first end 113, a second end 115 and a shaft 117 extending from the first end 113 to the second end 115, and has an outer surface 119. Except as otherwise specified herein, the outer surface 117 of the bone fastener 111 has a smooth or even configuration such that bone fastener 111 may easily pass through tissue. Other configurations are possible. For example, it is contemplated that all or a part of the outer surface 119 may be rough, textured, porous, semi-porous, dimpled and/or polished.

The first ends 113 of the bone fasteners 111 are removably connected to the horizontal strut 103 to define a bone graft cavity (see, for example, FIG. 5, as discussed further below). The first end 113 defines an open loop, such as, for example, a head 121 that has the shape of a partial toroid such that the horizontal strut 103 can be located or 'snapped' onto the head 121. The head 121 defines a curved or arcuate surface 123 that includes a reaction surface 125 (see also FIG. 2) that is linear and has the shape of a chord of a circle. The reaction surface 125 is aligned with the axes a and b and interacts with a corresponding portion of the outer surface 119 of the horizontal strut 103 to allow the head 121 to support and vertically retain the horizontal strut 103. The structure and function of the reaction surface 125 of the head 121 is discussed in further detail below.

The head 121 of the bone fastener 111 includes a prong 127 extending from the shaft 117 and terminating in a reaction surface 129, and a prong 131 extending from the shaft 117 and terminating in a reaction surface 133 disposed opposite the reaction surface 129 of the prong 127. The prongs 127, 131 extend more than halfway around the horizontal strut 103 to capture and detachably hold the horizontal strut 103 at the first end of the bone fastener 111. The structure and function of the prongs 127, 131 and the reaction surfaces 129, 133 thereof is discussed in greater detail below.

In addition to, and/or as an alternative to, the prongs 127, 131 of the head 121, it is envisioned that the horizontal strut 103 may be detachably coupled to the bone fastener 111 via clips, hooks, rings, female/male mating parts, snaps, spring bias and/or pressure fit. It is further envisioned that the head 121 may be sized and/or include an insert for a friction engagement with the outer surface 119 to fix the position and/or orientation of the horizontal strut 103 relative to the bone fastener 111.

It is contemplated that the bone augmentation device 101 may include one or a plurality of bone fasteners 111. It is further contemplated that the bone fasteners 111 may be disposed in a non-parallel relationship such as angularly offset, converging, diverging, and/or may be monolithically formed with the horizontal strut 103 or integrally attached thereto. It is envisioned that all or a portion of the bone fastener 111 may be flexible or plastically deformable such that the bone fastener 111 is adjustable or can be modified to conform to a selected portion of jawbone for a particular surgical application. It is further envisioned that the bone fastener 111 may be formed from a rigid or semi-rigid material to increase strength of bone augmentation device 101 and/or the integrity of a bone graft cavity (see, for example, FIG. 5, as discussed further below).

The second end 115 of the bone fastener 111 includes a sharpened tip 135 and an external thread 137. The sharpened tip 135 and the external thread 137 are cooperatively configured and dimensioned such that the bone fastener 111 is self-tapping or in the alternative is configured with threads so as to thread into a pre-drilled bore. In the self-tapping embodiment of the present invention, the pointed tip 135 and the external thread 137 permit the bone fastener 111 to readily penetrate bone tissue and achieve fixation with a jawbone to mount the bone augmentation device 101 with a selected portion of a jawbone at a surgical site according to the requirements of the jaw anatomy and/or a particular application, and to define a bone graft cavity (see, for example, FIG. 5, as discussed further below) at such surgical site with the horizontal strut 103 and the shafts 117 and heads 121 of the bone fasteners 111. Other configurations for the second end 115 of the bone fastener 111 are possible, such as, for example, alternative embodiments of the bone fastener 111 in accordance with the principles of the present disclosure in which the second end 115 has a tip that is not sharpened, and/or in which the second end 115 is configured and dimensioned such that the bone fastener 111 is not self-tapping. In at least some such embodiments, the second end 115 of the bone fastener 111 is threaded to conform to a pre-drilled hole. Still other configurations for the second end 115 of the bone fastener 115 are possible, such as, for example, alternative embodiments of the bone fastener 111 in accordance with the principles of the present disclosure in which the second end 115 is non-threaded. Still further configurations are possible.

The bone fasteners 111 are selectively capable of being moved or reoriented so as to extend toward the horizontal strut 103 from or along any one or more of multiple directions (two of which are shown in FIG. 1) through an angle $\alpha_1$. The significance of such flexibility of orientation or positioning of the bone fasteners 111 relative to the horizontal strut 103 will be discussed in greater detail below.

Figure 2:
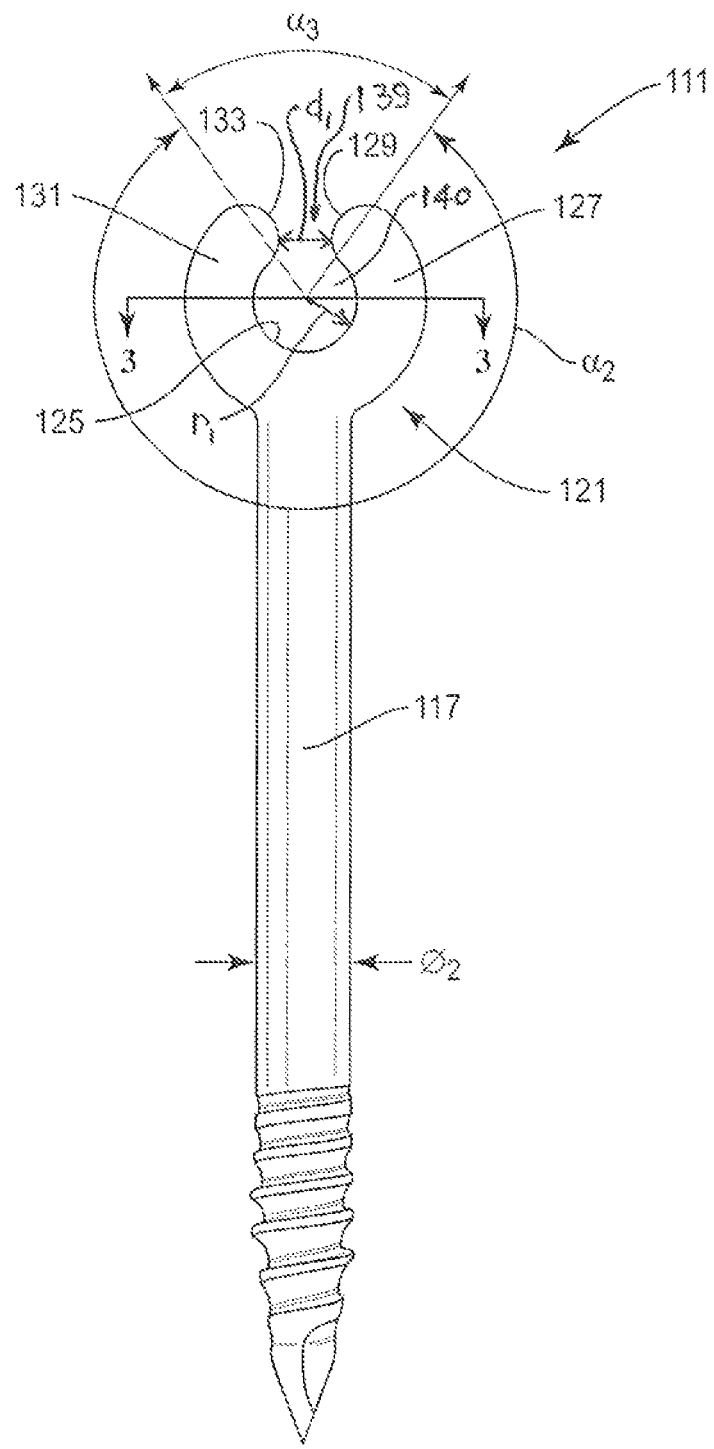
FIG. 2 is a front plan view of a bone fastener of the bone augmentation device shown in FIG. 1.

Turning now to FIG. 2, one of the bone fasteners 111 is shown in isolation from the remainder of the bone augmentation device 101 of FIG. 1. The bone fasteners 111 are fabricated from a biologically absorbable material, and/or a biodegradeable material that resorbs over time in vivo. Examples of such include, but are not limited to, polyglycolide, polylactide, polycaprolactone, poly(ethylene glycol), polyurethanes, polyfumarates, polyacrylamides, collagen, silk, polyamines, polysaccharides, tissue or tissue products, and copolymers and blends thereof.

The shaft 117 of the bone fastener 111 has a solid, cylindrical configuration and has a thickness, such as, for example, diameter $\phi_2$. In one embodiment, diameter $\phi_2$ is in a range of approximately 1 to 3 mm. Other configurations are possible. For example, the cross-sectional geometry of the shaft 117 of the bone fastener 111 may have various configurations, such as, for example, round, oval, oblong, triangular, polygonal having planar or arcuate sides, irregular, uniform, non-uniform, consistent or variable, and/or all or a portion of the bone fastener 111, including but not necessarily limited to the shaft 117, may be porous, perforated, tubular or articulate.

As shown in FIG. 2, the reaction surface 125 of the head 121 of the bone fastener 111 is a chord of a circle of radius $r_1$ that extends through an angle $\alpha_2$. For purposes of the present disclosure, and disregarding (for present purposes at least) the contours and dimensions of the reaction surfaces 129, 133 of the prongs 127, 131, the remainder of such circle, represented in FIG. 2 by an angle $\alpha_3$, may be considered to be the extent to which the loop formed by the head 121 of the bone fastener 111 is open. Alternatively, and/or in addition, a distance $d_1$ by which the reaction surfaces 129, 133 of the prongs 127, 131 are separated may be considered to be the extent to which the loop formed by the head 121 of the bone fastener 111 is open. In the embodiment of the bone augmentation device shown in FIG. 1, which includes the bone fastener 111 shown and discussed thus far with reference to FIGS. 1 and 2, the radius $r_1$ is approximately 0.5 mm to approximately 1.5 mm, the distance d1 is approximately 0.5 mm to approximately 1.5 mm, the angle $\alpha_2$ is approximately 300°, and the angle $\alpha_3$ is approximately 60°. Other values for the radius $r_1$, the distance $d_1$, the angle $\alpha_2$, and the angle $\alpha_3$ are possible.

The separation between the reaction surfaces 129, 133 of the prongs 127, 131 creates or defines an opening 139 in the head 121 for receiving the horizontal strut 103 (FIG. 1). The reaction surface 125 and the prongs 127, 131 create or define a socket 140 configured and dimensioned to allow the horizontal strut 103 to locate on or be captured by the head 121. The prongs 127, 131 and the reaction surfaces 129, 133 are configured and dimensioned to allow the horizontal strut 103 to conveniently pass downward through the opening 139, and to be retained or captured within the socket 140. Any one, or more than one, or all of the radius $r_1$, the distance $d_1$, the angle $\alpha_2$, and the angle $\alpha_3$ may change, either temporarily or non-temporarily, as the horizontal strut 103 (FIG. 1) is inserted through the opening 139 and/or snap-fit into the socket 140, as necessary or as desired for the convenience of the medical practitioner. Accordingly, the material properties and/or the initial structural dimensions of the prongs 127, 131 may be defined or selected so as to impart an appropriate degree of elasticity or flexibility to the head 121 to allow the horizontal strut 103 (FIG. 1) to be inserted through the opening 139 and/or captured in the socket 140.

Figure 3:
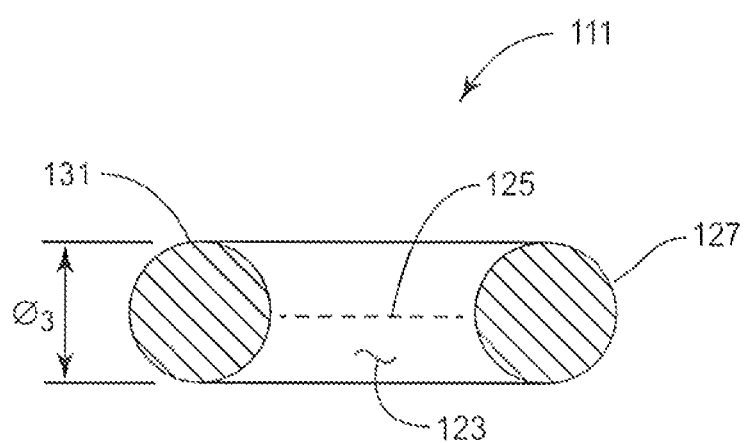
FIG. 3 is a top view in part cross section of the bone fastener of FIG. 2.

Referring now to FIG. 3, a portion of the arcuate surface 123 of the bone fastener 111 is shown in top view. As also shown in FIG. 3, the reaction surface 125 is substantially curvilinear in configuration, and each of the prongs 127, 131 has a solid configuration that is in the shape of a full circle in cross-section, and has a thickness, such as, for example, diameter $\phi_3$. In one embodiment, diameter $\phi_3$ is in a range of approximately 1 to 3 mm. Other configurations are possible in accordance with the present disclosure.

Referring to FIGS. 4-11, in assembly, operation and use, the bone augmentation device 101 is employed with a surgical procedure for treating periodontal disorders in a surgical repair and/or reconstruction procedure. For example, the bone augmentation device 101 can be employed to repair a defect and/or build up bone height and/or width of jawbone in a ridge augmentation procedure. Such augmentation can be used to provide sufficient bone for embedding and retaining an implant. The bone augmentation device 101 prevents overlying soft tissue and muscle from compressing new forming bone. The bone augmentation device 101 may also be employed with other surgical procedures for treatment of other periodontal diseases and/or bone disorders of other portions of a patients anatomy.

Figure 4:
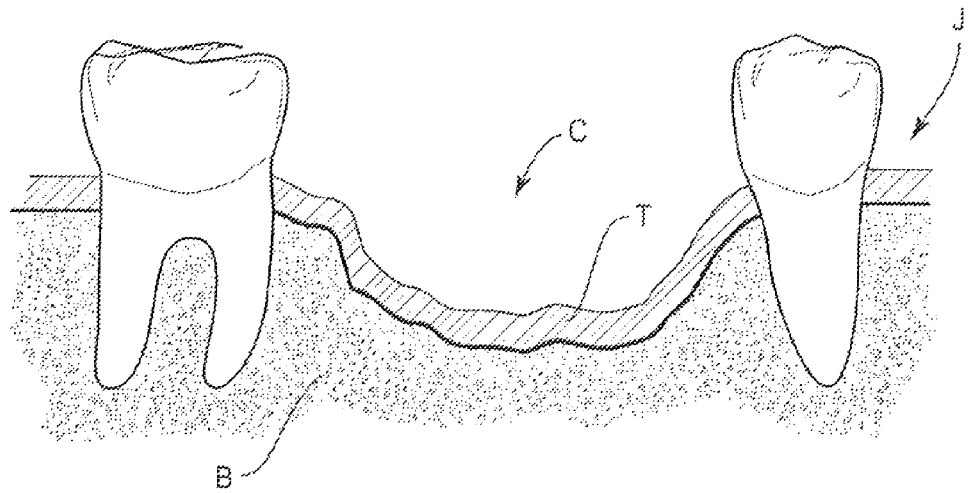
FIG. 4 is a side cutaway view in cross section of a jawbone.

In use, and referring now specifically to FIG. 4, to treat a section of a jaw J at a surgical site in accordance with the devices and methods of the present disclosure, a medical practitioner obtains access to the surgical site including the jaw J in any appropriate manner. The section of the jaw J at the surgical site includes gingival soft tissue T and bone tissue B. A cavity C of the bone B corresponds to a defect or disorder in need of treatment. As shown in FIG. 4, the gingival soft tissue T at the surgical site generally covers or overlays the bone B, both within and without the cavity C.

Figure 5:
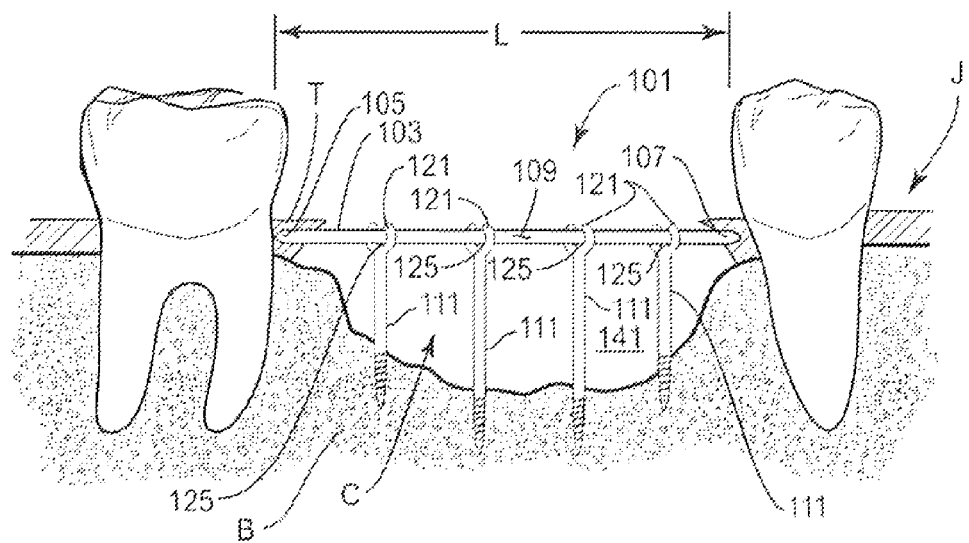
FIG. 5 is a side cutaway view in part cross section of the bone augmentation device shown in FIG. 1 and the jawbone shown in FIG. 2.

Turning now to FIG. 5, the gingival soft tissue T is retracted to expose a portion of the bone B suffering from defect and/or disorder including bone and/or tooth loss. The cavity C of the bone B that corresponds to the defect or disorder is mechanically debrided with an instrument (not shown) to remove infection and/or defect including granulation, soft tissue and bone matter. The surfaces of the jaw J at the surgical site are cleaned.

The bone augmentation device 101 is provided for mounting with the bone B adjacent the cavity C to add bone height and width to the jaw J. The bone fasteners 111 are connected with the horizontal strut 103 such that outer surface 109 of the horizontal strut 103 is securely retained by the reaction surface 125 of the heads 121 of the bone fasteners 111, as discussed above. The bone fasteners 111 are positioned in alignment with the cavity C for fixation with the tissues of the jaw J. Each end 105, 107 of the horizontal strut 103 may include a gripping surface to facilitate fixation with tissue. The gripping surface may be knurled, rough, textured, dimpled, and/or include ribs, teeth and prongs, and/or may be coated with adhesive. It is contemplated that ends 105, 107 may have various configurations for fixation with tissue such as a rod, pin, spike, threaded and/or may be configured for drilling and/or hammering. It is further contemplated that one or both ends 105, 107 of the horizontal strut 103 may be disposed to attach with, terminate in and/or for unrestricted movement within gingival tissue T.

The bone fasteners 111 are oriented with the horizontal struts 103, as described above, to form a scaffold configuration for the bone augmentation device 101 that defines a bone graft cavity 141. The scaffold configuration of the bone graft cavity 141 so defined can be selectively dimensioned and configured according to the particular surgical application. In accordance with embodiments of the present disclosure, the scaffold configuration of the bone augmentation device 101 maintains space between new forming bone and tissues of the jaw. The bone graft cavity 141 is disposed between the horizontal strut 103 and a selected portion of the jawbone at the surgical site.

The bone fasteners 111 are movable relative to the horizontal strut 103, and vice-versa, to selectively define the configuration and dimensions of the bone graft cavity 141. The bone fasteners 111 are selectively movable along the horizontal strut 103, in the direction shown by arrows A in FIG. 1, such that a length L, of the bone graft cavity 141, corresponding at least roughly to the length I of the horizontal strut 103, is defined. The horizontal strut 103 is selectively movable with regard to the distance by which the bone fasteners 111 are spaced apart. The bone fasteners 111 are selectively capable of being moved or reoriented so as to extend toward the horizontal strut 103 from any one or more of multiple directions (two of which are shown in FIG. 1) through the angle $\alpha_1$ (see FIG. 1).

The bone graft cavity 141 extends beyond the boundaries of the horizontal strut 103, including laterally or transversely, and potentially also longitudinally. Various dimensions and configurations of the surgical site, including a depth of the cavity C of the bone B that corresponds to the defect or disorder, may define the dimensions of the bone graft cavity 141. It is further contemplated that the horizontal strut 103 and the bone fasteners 111 can be adjusted and/or trimmed to the configuration and dimension requirements of a particular application.

Figure 6:
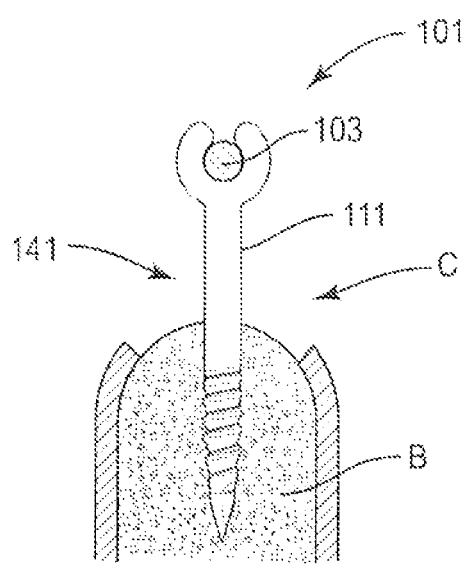
FIG. 6 is a front plan view in part cross section of the bone augmentation device and the jawbone shown in FIG. 5.
Figure 7:
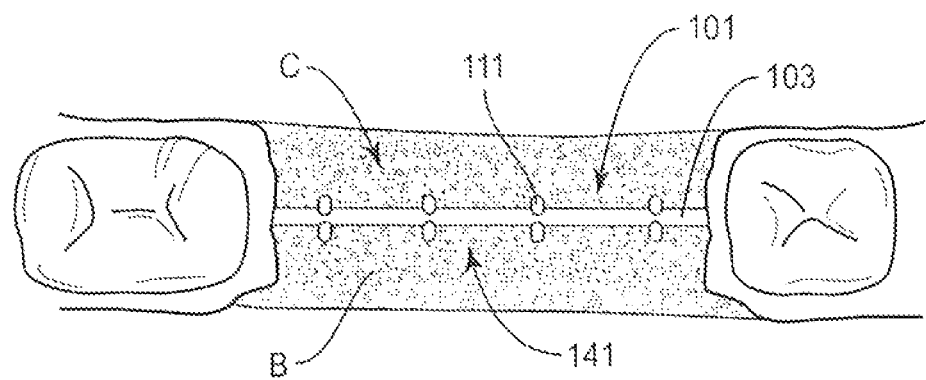
FIG. 7 is a top cutaway view of the bone augmentation device and the jawbone shown in FIG. 5.

As illustrated in FIGS. 6 and 7 the bone augmentation device 101 may be mounted in within the cavity C of the bone B such that the horizontal strut 103 extends longitudinally in parallel with the jawline and the horizontal strut 103 and the bone fasteners 111 are aligned within a vertical plane (not separately indicated) coinciding with a longitudinally extending centerline (not separately indicated) of the jaw J. It is envisioned that the horizontal strut 103 and the bone fasteners 111 are selectively movable to define various dimensions of a bone graft cavity 141 such as, for example, volume, perimeter, width and/or surface area to conform to a selected portion of a jawbone and/or for the requirements of a particular application.

Figure 8:
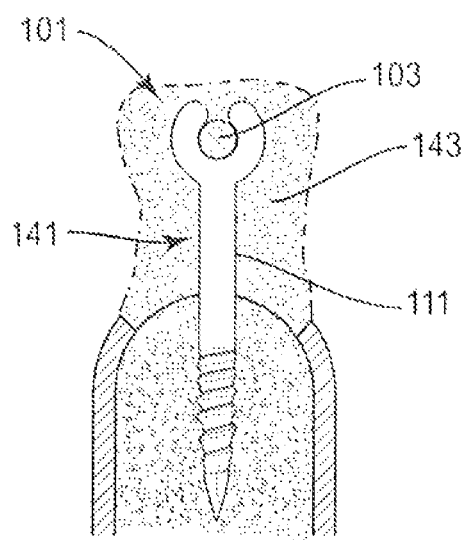
FIG. 8 is a plan view in part cross section of the bone augmentation device and the jawbone shown in FIG. 5 including bone graft.
Figure 9:
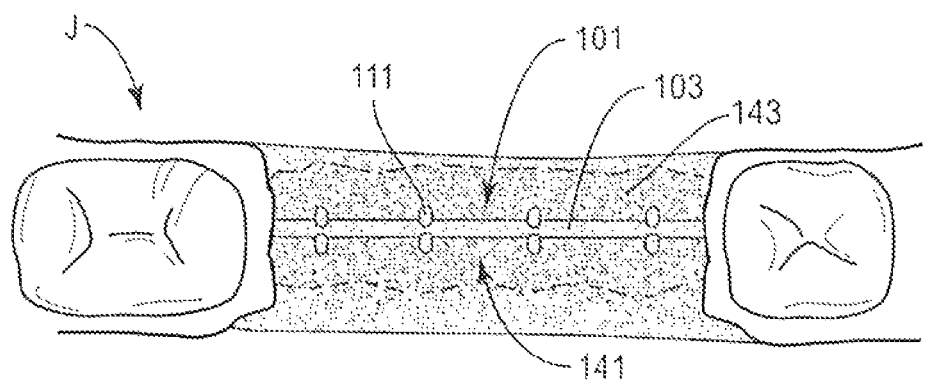
FIG. 9 is a top cutaway view of the bone augmentation device and the jawbone shown in FIG. 8.

As shown in FIGS. 8 and 9, the bone graft cavity 141 is configured for disposal of and includes bone growth promoting material, such as, for example, an appropriate quantity of bone graft 143 (FIG. 6) and/or other materials adjacent a jaw of a patient, which includes bone, cartilage or other tissues of the upper and lower jaw, gingiva, mandible and/or maxilla. It is envisioned that the bone graft 143 is composed of a particulate material, which may include an osteoconductive material such as hydroxyapatite and/or osteoinductive agent such as a bone morphogenic protein to enhance bone growth. It is further contemplated that the bone graft 143 and/or other materials disposed in a vicinity of the bone graft cavity 141 may extend beyond the bone graft cavity 141 and/or the perimeter or boundary established by the horizontal strut 103 and/or the bone fasteners 111.

It is contemplated that the bone graft 143 may include therapeutic polynucleotides or polypeptides, which can be packed or otherwise disposed in bone graft cavity 141. It is further contemplated that the bone graft 143 may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioabsorbable polymer that releases the biologically active agent or agents in an appropriate time dependent fashion as the polymer degrades within a patient. Suitable biologically active agents include, for example, bone morphogenic protein (BMP), Growth and Differentiation Factors proteins (GDF) and cytokines.

In one embodiment, a plurality of bone augmentation devices 101 of various configurations and dimensions, including both a plurality of horizontal struts 103 of various configurations and dimensions, and a plurality of bone fasteners 111 of various configurations and dimensions, is packaged as a system or kit that includes a bone growth promoting material in sufficient quantity to allow a practitioner to form a clinically efficacious bone graft such as the bone graft 143. In such an embodiment, the kit may include one or a plurality of dental prosthetics, implants, abutments and other materials for treatment.

In one embodiment, biologically active agents may be coated onto the exterior of one or all of the components of bone augmentation device 101 and/or applied thereto for gradual release such as by blending in a bioabsorbable polymer that releases the biologically active agent or agents in an appropriate time dependent fashion as the polymer degrades within a patient. Suitable biologically active agents include, for example, bone morphogenic protein (BMP) and cytokines.

One or all of the components of bone augmentation device 101, including the bone graft 143, may include one or a plurality of agents that can be configured as drug depots with medication for pain and may include antibiotics and/or therapeutics. It is envisioned that the agents may contain active agents and may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3), Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

Figure 10:
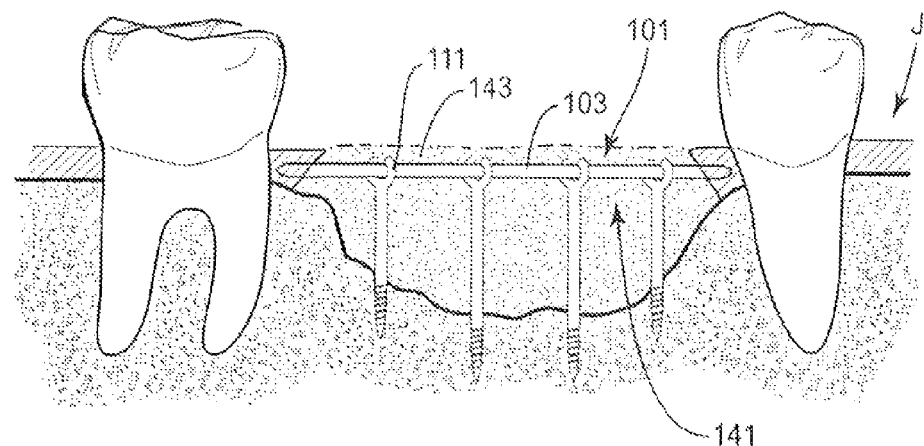
FIG. 10 is a side cutaway view in part cross section of the bone augmentation device and the jawbone shown in FIG. 8.

Referring to FIGS. 9-10, the bone augmentation device 101 includes the bone graft 143, described above, which is provided and injected within the scaffold configuration of the bone graft cavity 141 for treatment of the jaw J. The bone graft 143 is employed to promote bone growth to add bone height/width for dental implant retention. It is contemplated that a sufficient amount of the bone graft 143 is injected to occupy the bone graft cavity 141. It is further contemplated that additional bone graft and/or other material may be provided and/or coated with the components of the bone augmentation device 101. In one embodiment, bone graft 143 is installed with the horizontal strut 103 and the bone fasteners 111 in a desired configuration and dimension of the bone graft cavity 141 prior to mounting of the bone augmentation device 101 with the tissues of the jaw J.

Figure 11:
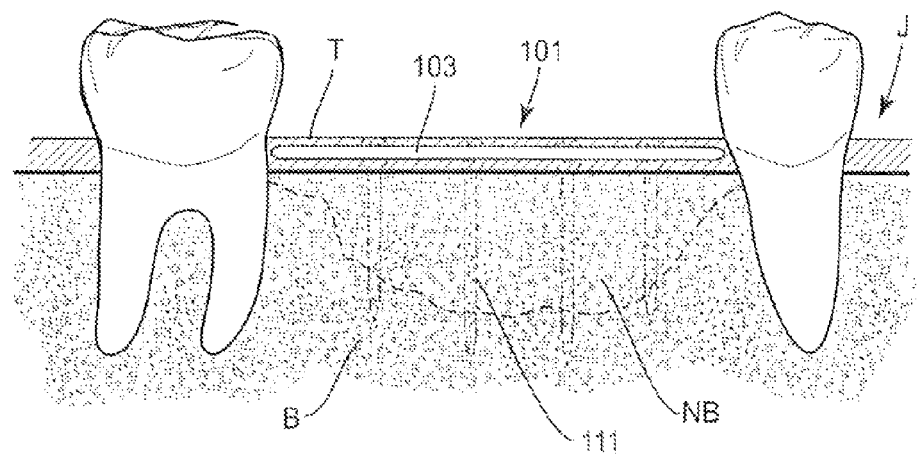
FIG. 11 is a side cutaway view in part cross section of the jawbone shown in FIG. 8.

Referring now to FIG. 11, over time, and with due care given to the surgical site in terms of appropriate hygiene and avoidance of undue mechanical stress and compression, new bone tissue NB grows in the bone graft cavity 141 (see FIG. 10), eventually completely replacing the bone graft 143 (see FIG. 10) previously contained within the bone graft cavity 141. As shown in FIG. 11, new bone tissue NB has filled the bone graft cavity 141 (see FIG. 10). The biodegradable material from which bone fasteners 111 (shown only in ghost line in FIG. 11) were formed has been fully and completely absorbed and displaced in vivo, both by newly formed bone NB in the region of the jaw J that previously constituted the cavity C (FIGS. 4 and 5), and within the deeper region of the jaw J associated with the healthy bone tissue B adjacent to the cavity C. The surgical site is accessed by a medical practitioner, and the horizontal strut 103 (shown only in ghost line in FIG. 11) is removed from the tissues of the jaw J. As discussed above, the diameter $\phi_1$ (FIG. 1) of the horizontal strut 103 has a relatively thin or reduced dimension such that the horizontal strut 103 may easily pass through the tissues of the jaw J including sliding passage through soft tissue and vessels of gingival soft tissue T that have grown over newly formed bone NB, as shown in FIG. 11. As such, the configuration of the bone augmentation device 101 (shown only in ghost line in FIG. 11) allows the horizontal strut 103 to be slid from the tissues of the jaw J with minimal tissue and vascular disruption.

Newly formed bone NB is provided to augment the pre-existing bone B in cavity C (see FIG. 4). As shown in FIG. 11, gingival tissue T may be retracted to expose new bone tissue NB, which can now support, for example, a dental implant. Due to the surgical treatment including the ridge augmentation employing bone augmentation device 101, the jaw J now includes sufficient bone including the new bone tissue NB and existing bone tissue B, for build up of bone height and width of the jawbone and/or retention of a dental implant (not shown). It is envisioned that the bone augmentation device 101 has provided new bone growth and sufficient stability to the jaw J such that subsequent procedures can be performed to attach a prosthetic, dental implant and abutment to the jaw J, and/or other treatments or procedures.

Figure 12:
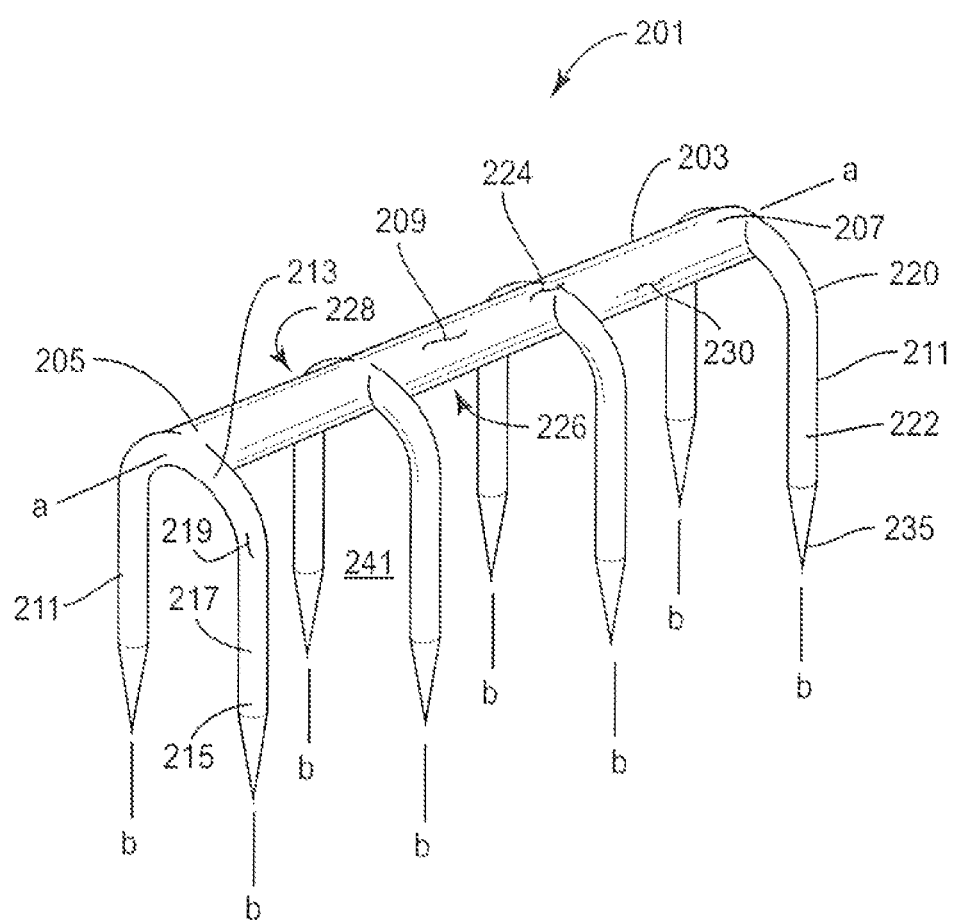
FIG. 12 is a perspective view of one embodiment of a bone augmentation device in accordance with the present disclosure.

In one embodiment, as shown in FIG. 12, a bone augmentation device 201 includes a horizontal beam 203. The horizontal beam 203 includes a first end 205 and a second end 207, and includes an outer surface 209. The horizontal beam 203 extends between the first end 205 and the second end 207 in an axial configuration, defining a longitudinal axis a.

The bone augmentation device 201 further includes a plurality of transverse members, such as, for example, vertical struts 211 for treating and conforming to a selected portion of a jawbone at a surgical site. Each of the vertical struts 211 includes a closed first end 213, an open second end 215, and a shaft 217 extending between the first end 213 and the second end 215 in an axial configuration. Each of the vertical struts 211 further includes an outer surface 219.

As shown in FIG. 12, the bone augmentation device 201 includes a longitudinally extending series of respective pairs of vertical struts 211. Within each such respective pair of vertical struts 211, the shafts 217 of the vertical struts 211 that compose such pair extend in different respective lateral directions (such as, for example, opposite lateral directions) away from the horizontal beam 203, and each such shaft 217 includes a respective bend or arcuate member 220 and a respective linear member 222 cooperatively configured and dimensioned such that the vertical strut 211 extends vertically downward to the second end 215 of the vertical strut 211, defining a transverse axis b.

As also shown in FIG. 12, between each pair of vertical struts 211 in the longitudinally-extending series thereof, the horizontal beam 203 includes an upper surface 224, a lower surface 226 opposite the upper surface 224, a side surface 228 adjacent the upper and lower surfaces 224, 226, and a side surface 230 opposite the side surface 228. The structure, function, and significance of the upper, lower, and side surfaces 224, 226, 228, 230 will be discussed in greater detail below.

Figure 17:
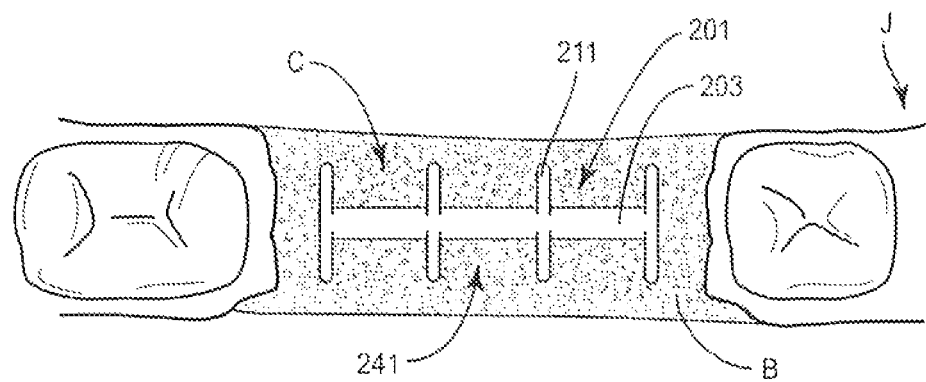
FIG. 17 is a top cutaway view of the bone augmentation device and the jawbone shown in FIG. 16.

The first ends 213 of the vertical struts 211 are fixedly coupled to the horizontal beam 203. The second end 215 of each vertical strut 211 includes a sharpened tip 235. The sharpened tip 235 is configured and dimensioned to permit each vertical strut 211 to readily penetrate bone tissue and achieve fixation with a jawbone to mount the bone augmentation device 201 with a selected portion of a jawbone at a surgical site according to the requirements of the jaw anatomy and/or a particular application, and to define a bone graft cavity 241 at such surgical site (see also, for example, as shown in FIG. 17, and as discussed further below) with the horizontal beam 203 and the shafts 217 of the vertical struts 211.

It is envisioned that all or a portion of each of members 220, 222 may be offset, staggered and/or disposed at an angle from the corresponding axes b. It is further envisioned that the axes b may be transverse to axis a and disposed at an orientation in a plurality of planes about the horizontal beam 203 including for example, perpendicular, acute, obtuse, and/or in a range between 0 and 360 degrees, according to the requirements of a particular application.

The linear members 222 are disposed in a parallel orientation and are spaced apart in a configuration to define the bone graft cavity 241 together with the arcuate members 220 and the horizontal beam 203. It is contemplated that the linear members 222 may be disposed in a non-parallel relationship such as angularly offset, converging, and/or diverging. It is contemplated that the vertical struts 211 may be monolithically formed with the horizontal beam 203 or separately formed therefrom and integrally attached thereto by means of an appropriate joining process, such as, for example, ultrasonic welding.

The outer surface 219 of each vertical strut 211 has a smooth or even configuration such that the vertical strut 211 may easily pass through tissue. It is contemplated that the outer surface 219 may be rough, textured, porous, semi-porous, dimpled and/or polished. The arcuate and linear members 220, 222 of the vertical struts 211 have a solid, cylindrical configuration and a thickness, such as, for example, diameter $\phi_3$. The diameter $\phi_3$ has a relatively thin or reduced dimension such that the arcuate and linear members 220, 222 may easily pass through tissue. It is envisioned that the diameter $\phi_3$ may be in a range of approximately 1 to 2 mm.

The vertical struts 211 are disposed in a parallel orientation and are spaced apart along the horizontal beam 203. The vertical struts 211 extend in a transverse orientation relative to longitudinal axis a to define the bone graft cavity 241 for treating and conforming to a selected portion of a jawbone at a surgical site. It is envisioned that the vertical struts 211 may include portions that extend in various orientations such as arcuate, undulating, orthogonal, stepped, staggered and/or intermittent with spaced apart ends.

It is contemplated that the bone augmentation device 201 may include one or a plurality of vertical struts 211. It is further contemplated that the vertical struts 211 may be disposed in a non-parallel relationship such as angularly offset, converging, or diverging. It is envisioned that all or a portion of each vertical strut 211 may be flexible or plastically deformable such that the vertical struts 211 are adjustable or can be modified to conform to a selected portion of jawbone for a particular surgical application. It is further envisioned that the vertical struts 211 may be formed from a rigid or semi-rigid material to increase strength of bone augmentation device 201 and/or the integrity of the bone graft cavity 241.

It is contemplated that the linear member 222 may include a gripping surface to facilitate fixation with the tissue surfaces including bone. It is contemplated that the second end 215 may includes a gripping surface to facilitate fixation with the tissue surfaces including bone. The gripping surface may be knurled, rough, textured, dimpled and/or include ribs, teeth and prongs, and/or may be coated with adhesive. It is further contemplated that the second end 215 may have various configurations such as a rod for fixation with tissues, a pin, or a spike.

The vertical struts 211 are spaced apart and extend from horizontal beam 203 to form a scaffold configuration that at least partially defines the bone graft cavity 241. The scaffold configuration of the bone graft cavity 241 can be selectively dimensioned and configured, for example by selective trimming of the bone augmentation device 201 at one or more points along the horizontal axis a. As discussed further below with respect to FIGS. 18, 19, and 20, the bone graft cavity 241 is configured for disposal of and includes bone graft similar to that described above.

The bone augmentation device 201, including the horizontal beam 203 and the vertical struts 211 thereof, are fabricated from a biologically absorbable material, and/or a biodegradeable material that resorbs over time in vivo. Examples of such include, but are not limited to, polyglycolide, polylactide, polycaprolactone, poly(ethylene glycol), polyurethanes, polyfumarates, polyacrylamides, collagen, silk, polyamines, polysaccharides, tissue or tissue products, and copolymers and blends thereof.

Figure 13:
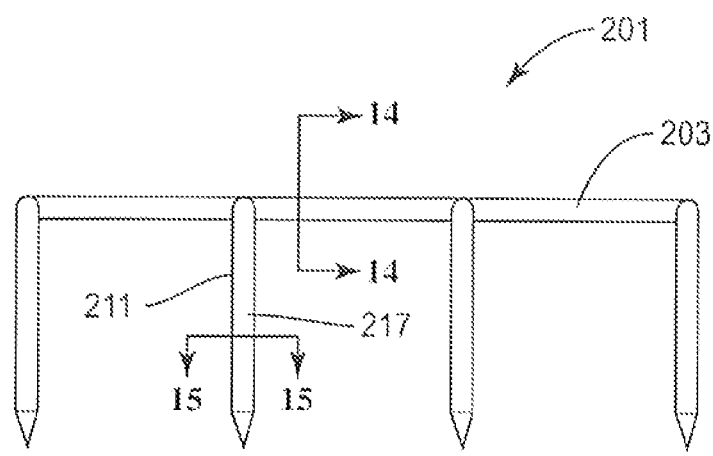
FIG. 13 is a side elevational view of the bone augmentation device shown in FIG. 12.

Turning now to FIG. 13, the bone augmentation device 201 of FIG. 12 is shown in side elevational view. As shown in FIG. 13, cross-sectional views of the horizontal beam 203, and of the shafts 217 of the vertical struts 211, are provided in FIGS. 14 and 15, respectively.

Figure 14:
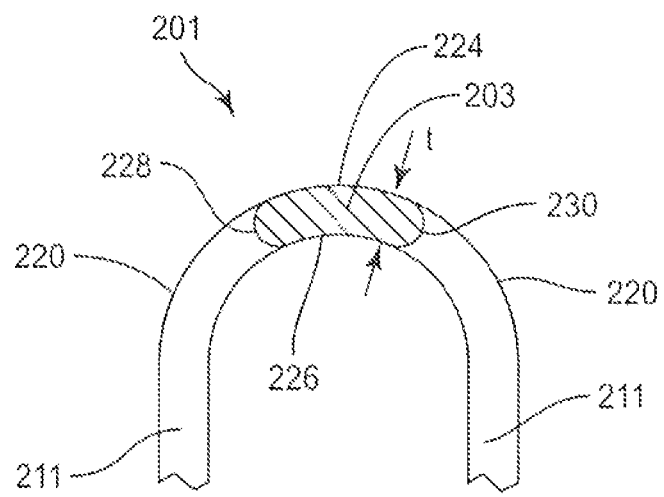
FIG. 14 is a front view in part cross section of the bone augmentation device shown in FIG. 12.

Turning to FIG. 14, the horizontal beam 203 of the bone augmentation device 201 is shown in a transverse cross-sectional view. The horizontal beam 203 has a laterally elongated solid configuration that is curved. The upper surface 224 is convex in shape, the lower surface 226 is convex in shape, and the side surfaces 228, 230 are smaller by comparison to the upper and lower surfaces 224, 226, but also convex in shape. Overall, the curvature of the upper and lower surfaces 224, 226 is dimensionally similar to that of the adjacent arcuate members 220 of the vertical struts 211 such that the arcuate members 220 and the horizontal beam 203 combine to form a shape of the upper portion of the bone augmentation device 201 that defines a semicircular arch in which the horizontal beam 203 has a constant thickness tin transverse cross-section. In one embodiment, the thickness t is in a range of approximately 1 to 3 mm. Other configurations are possible in accordance with the principles of the present disclosure.

Figure 15:
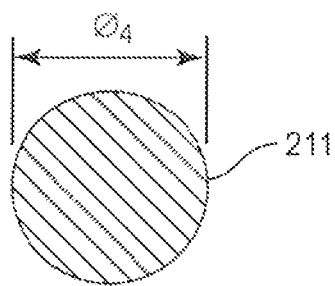
FIG. 15 is a top view in cross section of a vertical strut of the bone augmentation device shown in FIG. 12.

Referring now to FIG. 15, each of the vertical struts 211 has a solid configuration that is in the shape of a full circle in cross-section, and has a thickness, such as, for example, diameter $\phi_4$. In one embodiment, diameter $\phi_4$ is in a range of approximately 1 to 3 mm. Other configurations are possible in accordance with the principles of the present disclosure.

Figure 16:
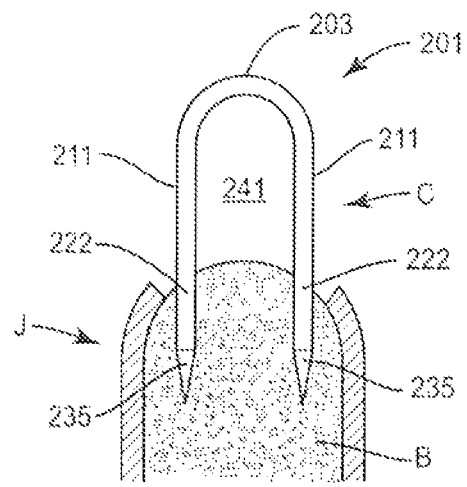
FIG. 16 is a plan view in part cross section of the bone augmentation device shown in FIG. 10 and the jawbone shown in FIG. 2.

Referring to FIGS. 16-21, in assembly, operation and use, the bone augmentation device 201 is employed with a surgical procedure for treating periodontal disorders in a surgical repair and/or reconstruction procedure, similar to that described with regard to FIGS. 2-9. The bone augmentation device 201 is provided for mounting with the bone B adjacent the cavity C to add bone height and width to the jaw J. The vertical struts 211 and the horizontal beam 203 are positioned in alignment with the cavity C for fixation with the tissues of the jaw J, as shown in FIGS. 16 and 17.

The length of the bone augmentation device 201 along the longitudinal axis a is trimmed if necessary to conform to the size of the cavity C for treatment thereof. Using an appropriate tool or tools, the medical practitioner drives the sharpened tips 235 of the linear members 222 to penetrate the bone B adjacent the cavity C for mounting of the bone augmentation device 201 with the jaw J in the desired configuration and dimension of the bone graft cavity 241.

Figure 18:
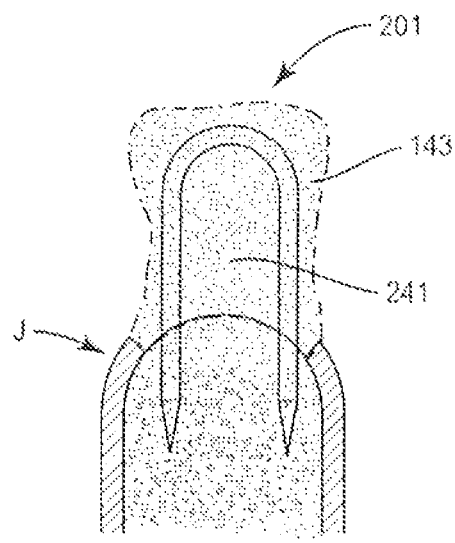
FIG. 18 is a plan view in part cross section of the bone augmentation device and the jawbone shown in FIG. 16 including bone graft.
Figure 19:
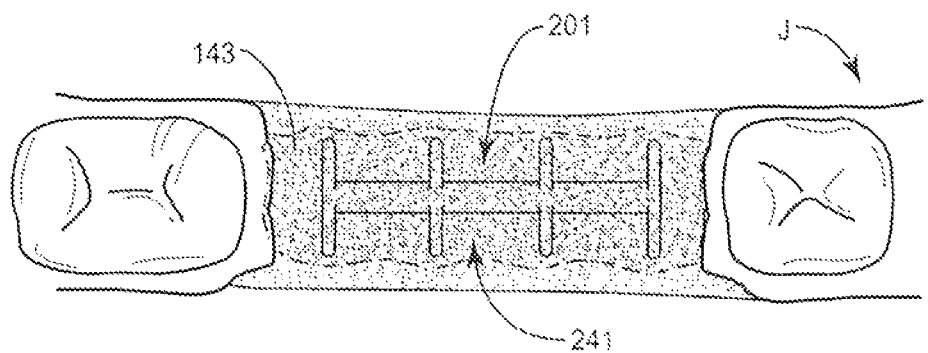
FIG. 19 is a top cutaway view of the bone augmentation device and the jawbone shown in FIG. 18.
Figure 20:
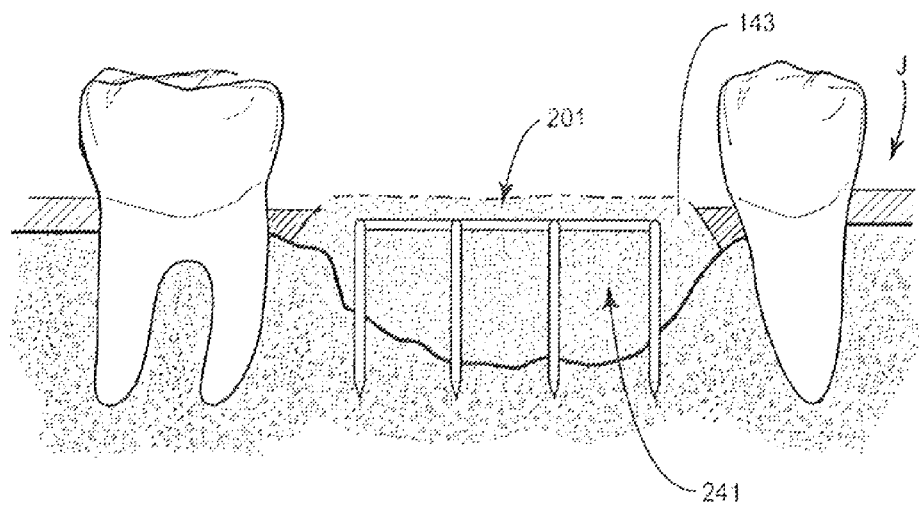
FIG. 20 is a side cutaway view of the bone augmentation device and the jawbone shown in FIG. 18.

Referring to FIGS. 18, 19, and 20, the bone augmentation device 201 includes bone graft 143, which is provided and injected within the scaffold configuration of the bone graft cavity 241 for treatment of the jaw J. Bone graft 143 is employed to promote bone growth to add bone height/width for dental implant retention.

Figure 21:
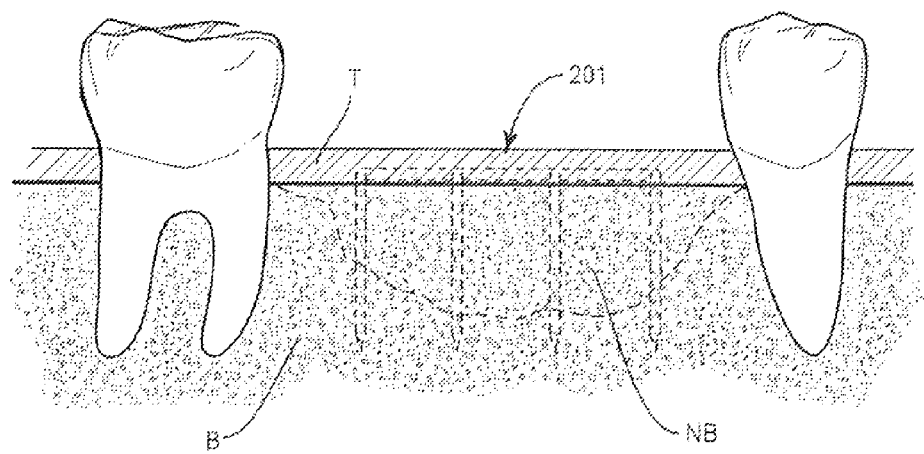
FIG. 21 is a side cutaway view in part cross-section of the jawbone shown in FIG. 18.

Turning now to FIG. 21, over time, and with due care given to the surgical site in terms of appropriate hygiene and avoidance of undue mechanical stress and compression, new bone tissue NB grows in the bone graft cavity 241 (see FIG. 16), eventually completely replacing the bone graft 143 (see FIG. 18) previously contained within the bone graft cavity 241. As shown in FIG. 21, new bone tissue NB has filled the bone graft cavity 241 (see FIG. 16). The biodegradable material from which the bone augmentation device 201 (shown only in ghost line in FIG. 21) was formed has been fully and completely absorbed and displaced in vivo, both by newly formed bone NB in the region of the jaw J that previously constituted the cavity C (see FIG. 4), and within the deeper region of the jaw J associated with the healthy bone tissue B adjacent to the cavity C (see FIG. 4). As such, any tissue and vascular disruption previously associated with the removal of bone augmentation devices or components thereof after the growth of new bone tissue NB is reduced, avoided, or eliminated.

Newly formed bone NB is provided to augment the pre-existing bone B in cavity C (see FIG. 4). Gingival tissue T may now be retracted to expose new bone tissue NB, which can now support, for example, a dental implant. Due to the surgical treatment including the ridge augmentation employing bone augmentation device 201, the jaw J now includes sufficient bone including the new bone tissue NB and existing bone tissue B, for build up of bone height and width of the jawbone and/or retention of a dental implant (not shown). It is envisioned that the bone augmentation device 201 has provided new bone growth and sufficient stability to the jaw J such that subsequent procedures can be performed to attach a prosthetic, dental implant and abutment to the jaw J, and/or other treatments or procedures Another embodiment of the present invention provides a method for augmenting surgical tissue at a particular site, i.e. a jawbone, by implanting at least one bone augmentation structure of the present invention into bone tissue so as to provide a cavity and structural support for depositing bone grafting material. Once implanted in place, bone-grafting material is deposited in and about the implanted structure. As new bone is formed underneath the bone augmentation implant, the bioabsorbable axial and transverse members of the augmentation implant are reabsorbed into the surrounding bone tissue. Any remaining non-absorbable members can be removed with minimal tissue and vascular disruption.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A bone augmentation device, comprising:
an axial member defining a longitudinal axis; and
a plurality of transverse members having a first end coupled to the axial member and extending from the first end to a second end configured for direct fixation with bone tissue, the transverse members each having a unitary construction and being spaced apart and disposed along the longitudinal axis in a transverse orientation relative thereto;
wherein the axial member and the transverse members are disposed in a configuration to define a bone graft cavity;
wherein the transverse members are formed of biologically absorbable material comprising a human allograft collagen and bone composite material with structural properties such that at least the transverse members are configured to form new bone around the bone augmentation device,
wherein the axial member is formed of human allograft collagen and bone composite materials with structural properties, a ceramic and collagen material with structural properties or a combination thereof,
wherein the second end of each transverse member is pointed and configured to facilitate insertion into the bone tissue.
2. The bone augmentation device of claim 1, wherein the axial member is an elongated strut.

3. The bone augmentation device of claim 1, wherein each of the transverse members extends from the axial member in a linear configuration.

4. The bone augmentation device of claim 1, wherein the first end of each transverse member is closed.

5. The bone augmentation device of claim 1, wherein the first end of each transverse member defines a closed loop configured to receive the axial member.

6. The bone augmentation device of claim 1, wherein the second end of at least one of the transverse members is threaded.

7. The bone augmentation device of claim 1, further comprising bone graft.

8. The bone augmentation device of claim 1, wherein each of the transverse members has a first end permanently affixed to the axial member.

9. The bone augmentation device of claim 1, wherein the transverse members are of unitary construction with the axial member.

10. The bone augmentation device of claim 1, wherein the transverse members are monolithically formed with the axial member.

11. A bone augmentation device, comprising:
an axial member defining a longitudinal axis; and
a plurality of transverse members having a first end coupled to the axial member and extending from the first end to a second end configured for direct fixation with bone tissue, the transverse members each having a unitary construction and being spaced apart and disposed along the longitudinal axis in a transverse orientation relative thereto;
wherein the axial member and the transverse members are disposed in a configuration to define a bone graft cavity;
wherein the transverse members are formed of biologically absorbable material comprising a human allograft collagen and bone composite material with structural properties such that at least the transverse members are configured to form new bone around the bone augmentation device,
wherein the axial member is formed of human allograft collagen and bone composite materials with structural properties, a ceramic and collagen material with structural properties or a combination thereof,
wherein the second end of each transverse member is threaded and configured to facilitate penetration of bone tissue.

12. The bone augmentation device of claim 11, wherein the axial member is an elongated strut.

13. The bone augmentation device of claim 11, wherein each of the transverse members extends from the axial member in a linear configuration.

14. The bone augmentation device of claim 11, wherein the first end of each transverse member defines a closed loop configured to receive the axial member.

* * * * *